(12) United States Patent
Chen et al.

(10) Patent No.: US 7,862,536 B2
(45) Date of Patent: Jan. 4, 2011

(54) COMBINED NASAL SPRAY AND ASPIRATOR DEVICE

(75) Inventors: Kun Sung Chen, San-Chung (TW); Ying Chao Lin, San-Chung (TW); Kuo Hung Huang, San-Chung (TW); Ta Chieh Yang, San-Chung (TW)

(73) Assignee: Avita Corporation, Taipei County (TW)

( * ) Notice: Subject to any disclaimer, the term of this patent is extended or adjusted under 35 U.S.C. 154(b) by 225 days.

(21) Appl. No.: 11/958,955

(22) Filed: Dec. 18, 2007

(65) Prior Publication Data

US 2008/0312674 A1  Dec. 18, 2008

(30) Foreign Application Priority Data

Jun. 15, 2007 (TW) .............................. 96121684 A

(51) Int. Cl.
*A61M 1/09* (2006.01)
(52) U.S. Cl. ....................................................... 604/73
(58) Field of Classification Search .................. 604/35, 604/43, 77, 94.01, 73; 433/95, 87, 185
See application file for complete search history.

(56) References Cited

U.S. PATENT DOCUMENTS

| | | | | |
|---|---|---|---|---|
| 4,215,476 | A * | 8/1980 | Armstrong | 433/80 |
| 4,340,365 | A * | 7/1982 | Pisanu | 433/80 |
| 4,680,026 | A * | 7/1987 | Weightman et al. | 604/33 |
| 5,147,292 | A * | 9/1992 | Kullas et al. | 604/34 |
| 6,135,980 | A * | 10/2000 | Vu | 604/73 |
| 6,328,718 | B1 * | 12/2001 | Chiang et al. | 604/319 |
| 6,464,498 | B1 * | 10/2002 | Pond | 433/81 |
| 6,517,511 | B2 * | 2/2003 | Yao | 604/35 |
| 6,520,931 | B2 * | 2/2003 | Suh | 604/73 |
| 6,595,949 | B1 * | 7/2003 | Shapiro | 604/73 |
| 6,907,879 | B2 * | 6/2005 | Drinan et al. | 128/202.22 |
| 6,918,764 | B2 * | 7/2005 | Ito et al. | 433/91 |
| 7,143,763 | B2 * | 12/2006 | Abate | 128/200.14 |
| 7,160,273 | B2 * | 1/2007 | Greter et al. | 604/319 |
| D536,781 | S * | 2/2007 | Yanes et al. | D24/108 |
| 7,351,235 | B2 * | 4/2008 | Chiou | 604/319 |
| 2003/0225427 | A1 | 12/2003 | Chen | |

* cited by examiner

*Primary Examiner*—Nicholas D Lucchesi
*Assistant Examiner*—Diva Ranade
(74) *Attorney, Agent, or Firm*—Tim Tingkang Xia; Morris, Manning & Martin, LLP

(57) ABSTRACT

A combined nasal spray and aspirator device includes an air pump disposed within a housing and comprises a spray and aspirator assembly. The air pump, at which an air suction connector and an air discharge connector are disposed, is driven by a driving component to perform air suction and discharge actions. The spray and aspirator assembly, mounted to the air suction connector and the air discharge connector, comprises a spray conduit and a first aspiration conduit; the spray conduit connects to an atomizer which is provided with liquids from a liquid storage container, and the first aspiration conduit connects to a mucus collector so that when some air carrying mucus enters the mucus collector, the mucus is left behind and the air enters the air pump through a second aspiration conduit. The device of the present invention integrates the operations of a nasal spray and a nasal aspirator, sucking the mucus away right after it sprays and liquefies the mucus, with said actions occurring almost simultaneously. The present invention is physically more favorable for users.

14 Claims, 6 Drawing Sheets

COMBINED NASAL SPRAY AND ASPIRATOR DEVICE

BACKGROUND OF THE INVENTION

1. Field of the Invention

The present invention relates to a combined nasal spray and aspirator device, and more particularly to a combined nasal spray and aspirator device that requires detachment of neither a spray unit nor an aspirator unit.

2. Description of the Related Art

There are many nasal spray or nasal aspirator products on the market, as cleansing needs and medical care of nasal cavities are clinically important. Concerning personal health care, it is particularly necessary to provide simple and fast nasal care equipments that help suction nasal mucus or phlegm for patients. Preferably, such nasal care equipments can further provide nasal cavities, even throats or other wounds, with cleansing actions by spray or other means. Among the nasal care products, there are many designed for certain specific aim only. For example, a nasal aspirator is generally designed for suction of the patient's mucus, and a nasal spray is generally for delivering drugs into the nasal cavity. While some products try to combine an aspirator device and a spray device on the same instrument, these products still require the user to detach a spray device first in order to attach an aspirator device onto the instrument. Or the user may need to detach a connecting tube between the pump and the aspirator device in order to connect the pump and the spray unit. Some other products contain a wristband connected to the pump, which connects to the aspirator or the spray by a flexible tube. Generally, a conventional nasal care equipment integrating an aspirator and a spray performs the spray action first. However, it takes time to change the operable sub-units and may cause the mucus to flow out of the nasal cavity. It is inconvenient, therefore, for the user to operate the nasal spray and the nasal aspirator separately.

SUMMARY OF THE INVENTION

The main object of the present invention is to provide a device that combines the operations of a nasal spray and a nasal aspirator. By spraying on the nasal cavity first, the device liquefies the mucus within, and almost simultaneously, it sucks the mucus away. The design of the present invention is physically more favorable for users.

The nasal spray and aspirator device comprises a housing and a spray and aspirator assembly. The housing includes an air pump, at which an air suction connector and an air discharge connector are disposed. The air pump is driven by a driving component to complete the air suction and discharge operations. The spray and aspirator assembly is coupled to the air suction connector and the air discharge connector, comprising a spray conduit and a first aspiration conduit. The spray conduit connects to an atomizer, and some liquid is provided for the atomizer from a liquid storage container, wherein the liquid can be some water or therapeutic drug. The aspiration conduit connects to a mucus collector. When some aspirated air carrying mucus enters the mucus collector through the first aspiration conduit, the mucus will be left in the collector, with the air continuing its progression into the air pump through a second aspiration conduit.

The air pump comprises a valve, a cover portion, a joint portion, and a base portion. The valve includes an air suction hole having a first valve and an air discharge hole having a second valve, wherein the first valve is parallel to the second valve. An air suction connector and an air discharge connector are disposed at the cover portion, which further includes a connection socket for connecting with the valve so that the first valve spatially corresponds to the air suction connector, and the second valve spatially corresponds to the air discharge connector. The joint portion includes an air hole which links to a channel; the air hole spatially corresponds to the second valve, and one end of the channel spatially corresponds to the first valve. At the opposite side of the joint portion, a recess chamber is formed corresponding to the channel. A flexible plate is located at the base portion, which forms an air chamber altogether with the recess chamber.

The spray conduit and the first aspiration conduit of the present invention are arranged in parallel so as to have the nasal spray and the nasal aspirator operate almost simultaneously. Alternatively, in another embodiment of the present invention, the spray conduit and the first aspiration conduit are disposed concentrically. The device of the present invention integrates the operations of a nasal spray and a nasal aspirator, sucking the mucus away right after it sprays and liquefies the mucus, with said actions occurring almost simultaneously, or alternately and continually, or alternately and uninterruptedly. The present invention is physically more favorable for users.

DETAILED DESCRIPTION OF THE INVENTION

Figure 1:
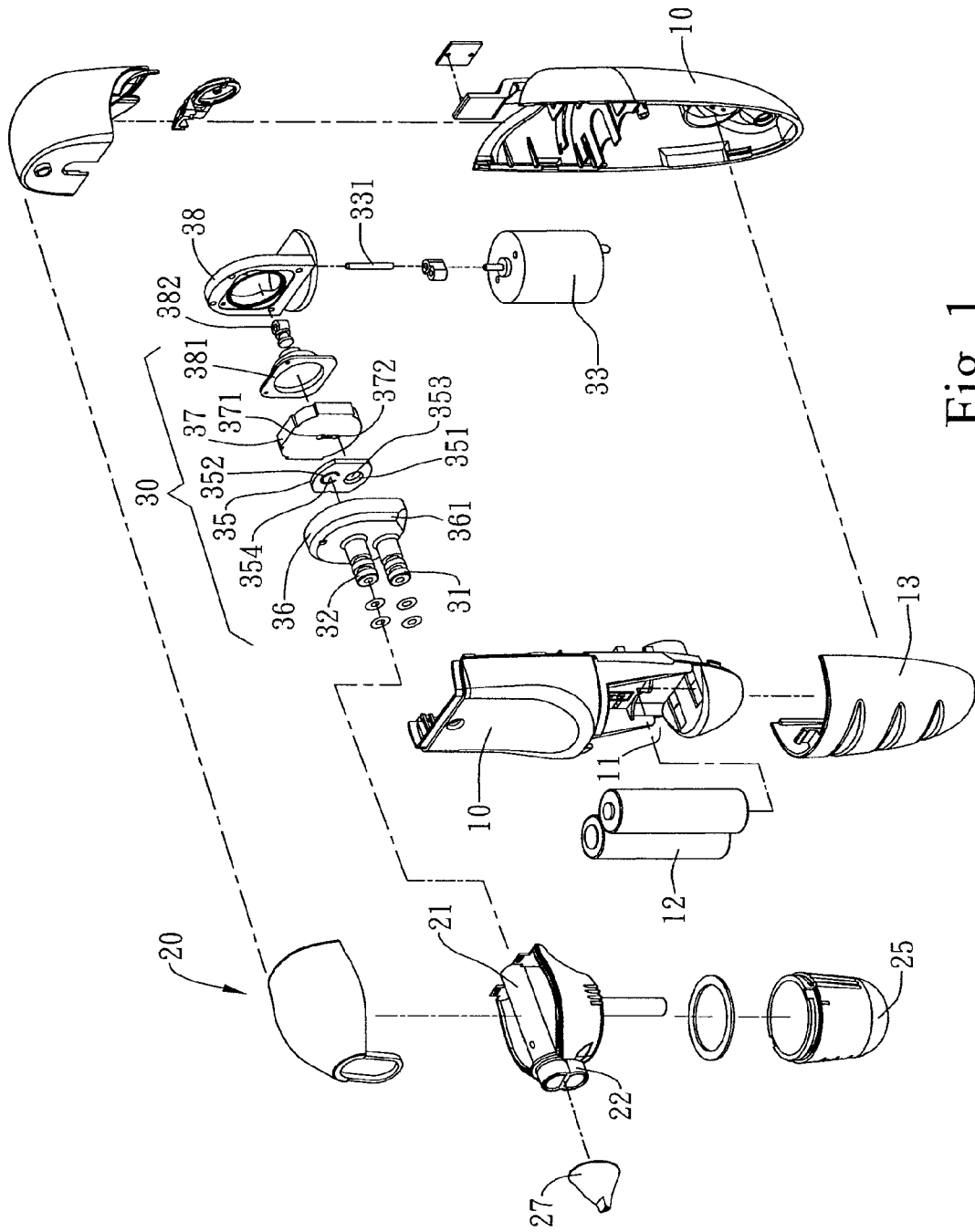
FIG. 1 is an exploded pictorial view of the combined nasal spray and aspirator device of the present invention.

Referring to FIG. 1, an exploded pictorial view of the combined nasal spray and aspirator device of the present invention is shown. The combined nasal spray and aspirator device comprises a housing 10 and a spray and aspirator assembly 20. An air pump 30 that can carry out air suction and discharge actions simultaneously is provided within the housing 10. An air suction connector 31 and an air discharge connector 32 are disposed at the air pump 30, which is driven by a driving component 33 to generate a suction and discharge force. When the air is drawn into the air chamber 34 within the air pump 30, through the air suction connector 31, the driving component 33 then forces the air pump 30 to expel the air, through the air discharge connector 32. The driving component 33 is a motor.

Figures 2, 3:
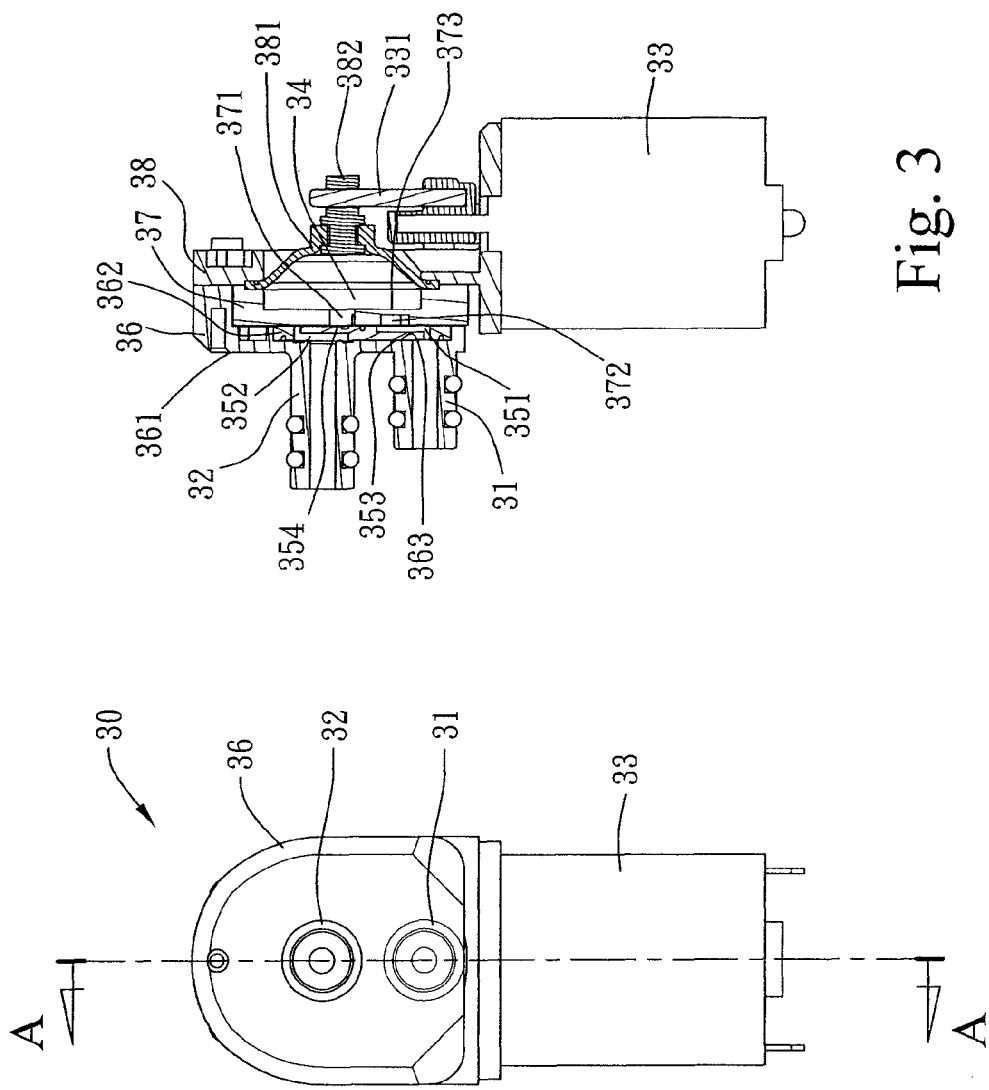
FIG. 2 is a schematic view of the air pump of the combined nasal spray and aspirator device of the present invention.
FIG. 3 is a cross-sectional view of the air pump of the combined nasal spray and aspirator device of the present invention.

Referring to FIGS. 1 to 3, an exploded pictorial view of the combined nasal spray and aspirator device, a schematic view of the air pump, and a cross-sectional view of the air pump in the present invention are shown respectively. The air pump 30 comprises a valve 35, a cover portion 36, a joint portion 37, and a base portion 38. The valve 35 includes an air suction hole 351 having a first valve 353, and an air discharge hole 352 having a second valve 354, wherein the first valve 353 and the second valve 354 are disposed in parallel. The cover portion 36 includes a first surface 361 and a second surface 362, the first surface 361 containing the air suction connector 31 and the air discharge connector 32. The second surface 362 has a connection socket 363 corresponding to the air suction connector 31 and the air discharge connector 32 for attaching the valve 35 so that the valve 35 can be fixed in the connection socket 363. As a result, the first valve 353 spatially corresponds to the air suction connector 31, and the second valve 354 spatially corresponds to the air discharge connector 32. The air is under control in this manner, entering the air suction connector 31 in one direction and going out of the air discharge connector 32 in the other direction.

The joint portion 37 has an air hole 371, which spatially corresponds to the second valve 354 and links to a channel 372 disposed on the joint portion 37, and therefore, one end of the channel 372 corresponds to the first valve 353. This disposition enables the air to pass through the air hole 371. At the opposite side of the joint portion 37, a recess chamber 373 is located on the other end of the channel 372. The base portion 38 is fastened to the recess chamber 373 and altogether they form an air chamber 34; more specifically, a flexible plate 381 on the base portion 38 and the recess chamber 373 form the air chamber 34. The flexible plate 381 connects to a pivot joint 382 which, at the same time, pivotally connects to an eccentric shaft 331 linking to the driving component 33. When the driving component 33 drives the shaft 331 to compress the flexible plate 381, the air can be sucked in and then expelled out through the air hole 371.

In sum, the air enters the suction connector 31, passes through the first valve 353 and the channel 372, and comes into the air chamber 34 through the air hole 371. Subsequently, the air is compressed by the flexible plate 381, goes out from the air hole 371, passes through the second valve 354, and is then discharged by the air discharge connector 32.

Figure 4:
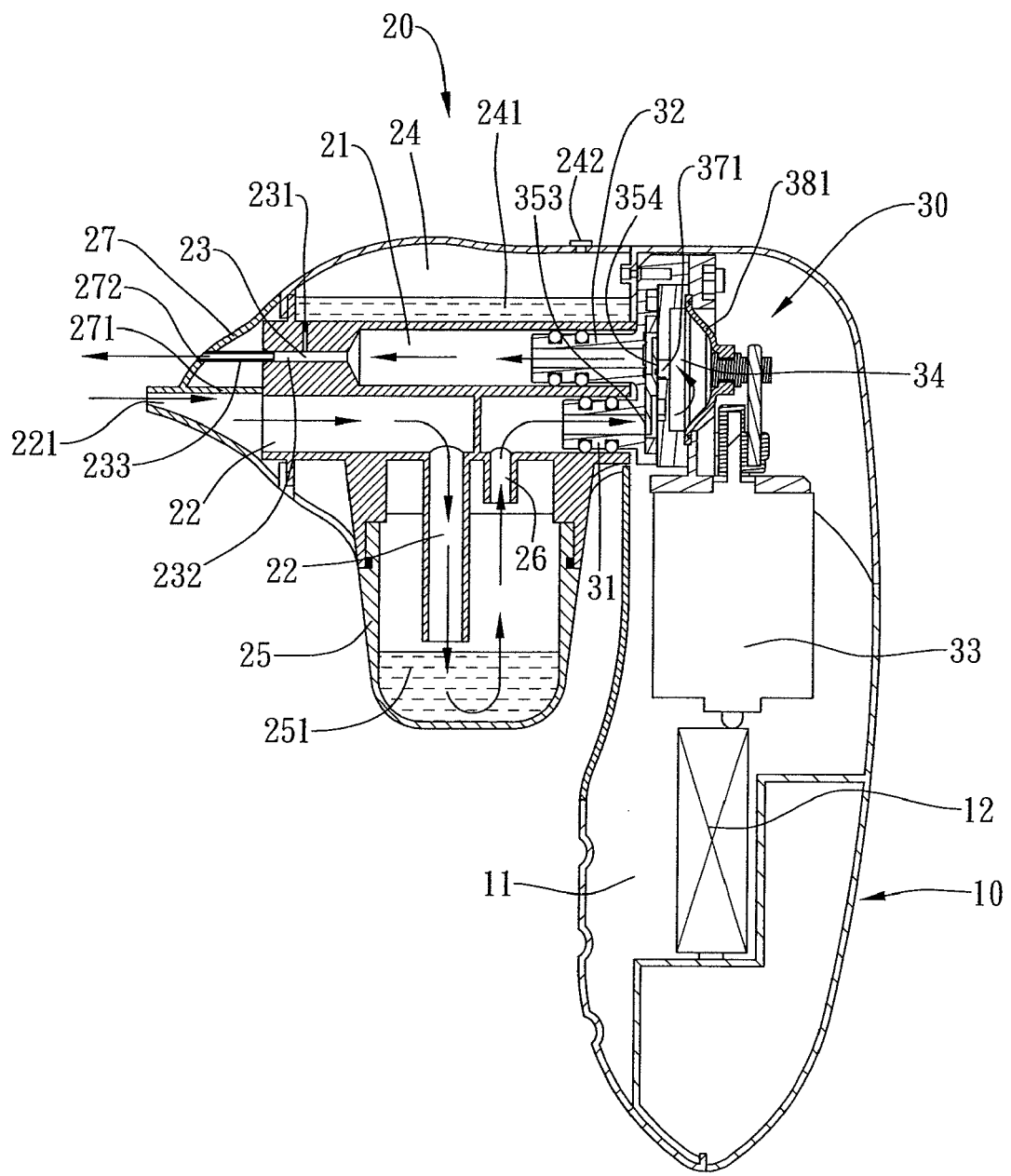
FIG. 4 is a cross-sectional view of the combined nasal spray and aspirator device according to a first embodiment of the present invention.

Referring to FIG. 4, a cross-sectional view of the combined nasal spray and aspirator device according to a first embodiment of the present invention is shown. The spray and aspirator assembly 20, comprising a spray conduit 21 and a first aspiration conduit 22, is attached to the air suction connector 31 and the air discharge connector 32. The spray conduit 21 connects to an atomizer 23, and liquid 241 is provided for the atomizer 23 from a liquid storage container 24. The first aspiration conduit 22 connects to a mucus collector 25 so that when the air carrying mucus passes through the mucus collector 25, it is left within the collector and the air continues its progression into the pump 30 through a second aspiration conduit 26. The liquid 241 within the liquid storage container 24 can be some water or therapeutic drug. The liquid storage container 24 has a filling inlet 242 for filling therapeutic drug or liquid at any time.

A power chamber 11 for placing a battery 12 is located within the housing 10 and is covered with a lid 13.

The spray conduit 21 and the first aspiration conduit 22 are positioned alongside. When the driving component 33 drives the flexible plate 381, the flexible plate 381 begins performing the air suction and discharge actions. When a suction action is generated, external air with or without mucus enters the mucus collector 25 through the first aspiration conduit 22. Then, the mucus 251, which is the dirty liquid part, is left behind, and the clean air keeps going through the second aspiration conduit 26, the first valve 353, and the air hole 371 in order to enter the air chamber 34. The air sucked in generally contains mucus or other unclean substances, and thus, it is necessary to treat the air first.

After being compressed by the flexible plate 381 and discharged from the air hole 371, the air enters the spray conduit 21 through the second valve 354. Subsequently, the air passes through the atomizer 23, causing the therapeutic drug or liquid to enter the spray conduit 21; then, the therapeutic drug or liquid is sprayed out into the nasal cavity and treatment is achieved. In fact, the air suction and discharge actions occur almost at the same time. The operation of the spray occurs right after that of the aspirator, spraying liquid into the nasal cavity almost simultaneously when the mucus is liquefied and sucked into the device and vice versa. The problem with a prior art device that the mucus flows out of the nasal cavity after the spray of liquid is then solved. The nearly simultaneous operation, or alternately and continually, or alternately and uninterruptedly of spray and aspiration, thus, is physically more favorable for users. Meanwhile, the mucus collector 25 in this embodiment is detachable for cleaning at any time.

A passage 231 is disposed between the atomizer 23 and the liquid storage container 24. With the application of Venturi principle, the therapeutic drug or liquid can be drawn into the spray conduit 21 through the passage 231 and can be sprayed out with the air. The atomizer 23 and the passage 231 are disposed at the front end of the spray conduit 21. The atomizer 23 has a liquid spray channel 232 within, wherein the internal diameter of the channel 232 is less than that of the spray conduit 21 and the liquid spray channel 232 communicates vertically with the passage 231.

Figure 5:
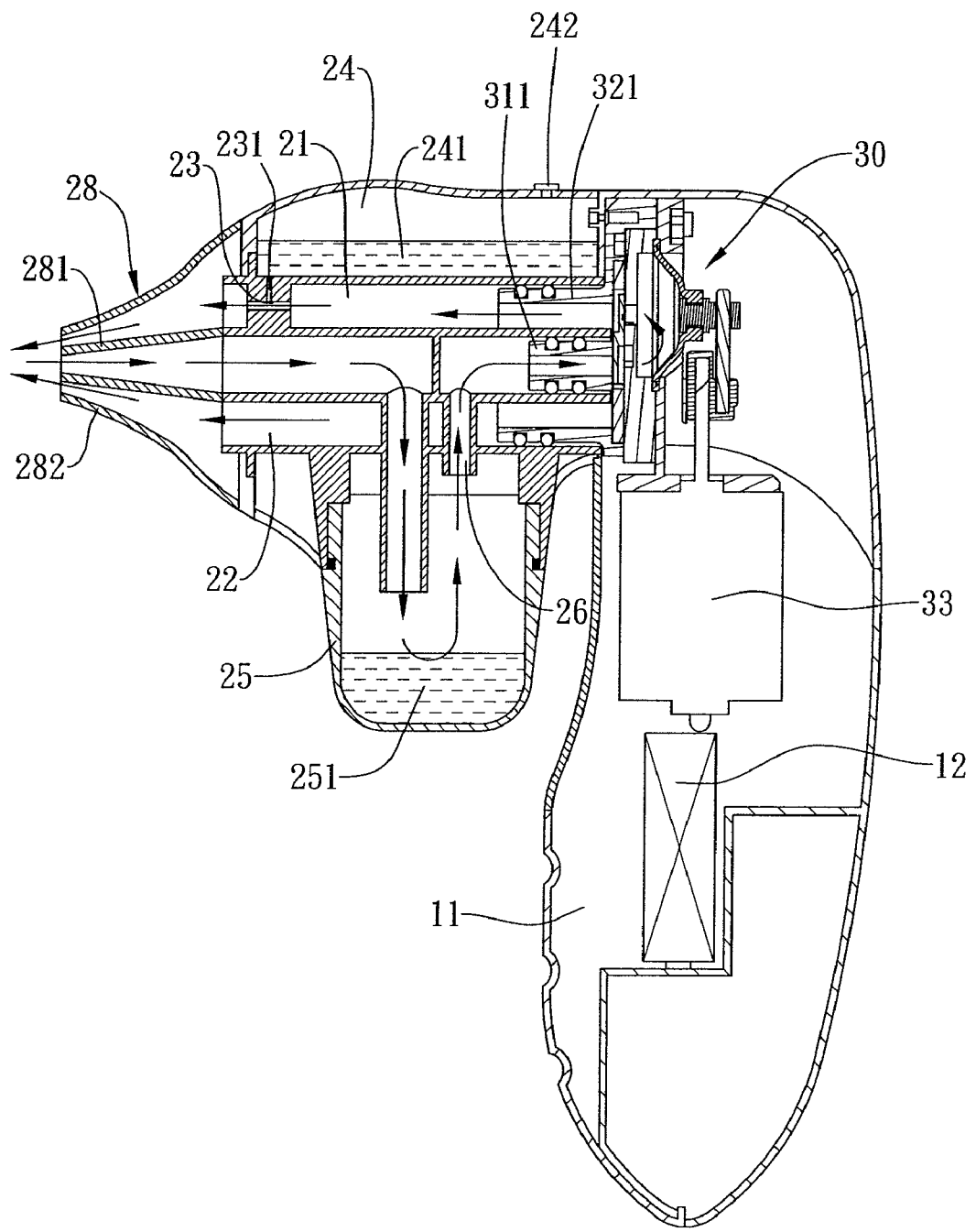
FIG. 5 is a cross-sectional view of the combined nasal spray and aspirator device according to a second embodiment of the present invention.
Figure 6:
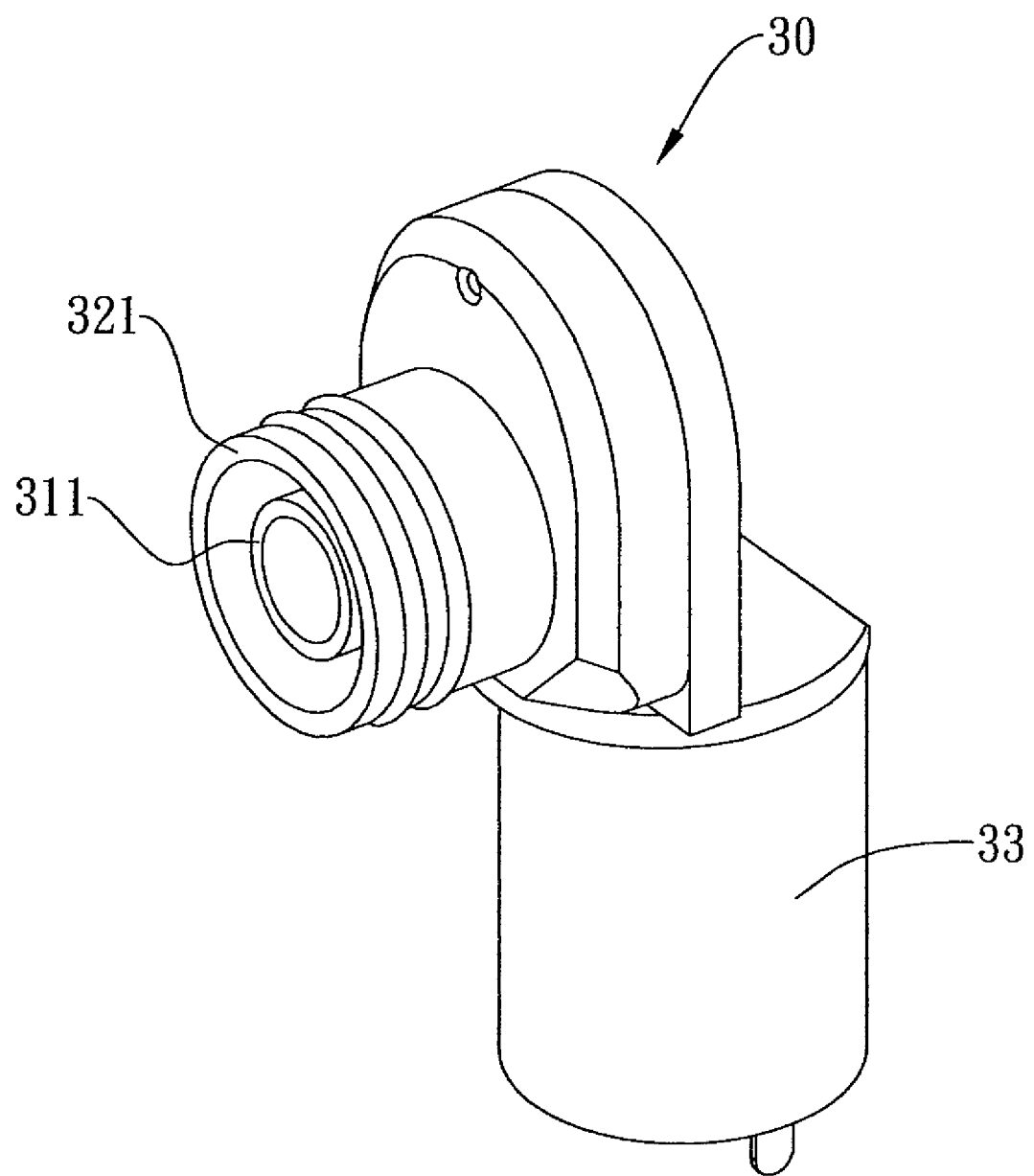
FIG. 6 is a schematic view of the air pump of the combined nasal spray and aspirator device according to a second embodiment of the present invention.

Referring to FIGS. 5 and 6, a cross-sectional view of the combined nasal spray and aspirator device and a schematic view of the air pump according to a second embodiment of the present invention are shown. The spray conduit 21 surrounds the first aspiration conduit 22, which means the air suction connector 311 is surrounded by the air discharge connector 321, as shown in FIG. 6. The first aspiration conduit 22 extends into the mucus collector 25, and the second aspiration conduit 26 extending from the mucus collector 25 connects to the air suction connector 311. When the driving component 33 drives the flexible plate 381, it begins the air suction and discharge actions. As air suction occurs, external air enters the mucus collector 25 through the first aspiration conduit 22. After leaving the mucus behind in the collector 25, the clean part of the air enters the second aspiration conduit 26 and goes into the air chamber 34 through the first valve 353 and the air hole 371.

After being compressed by the flexible plate 381 and discharged from the air hole 371, the air enters the spray conduit 21 through the second valve 354. Subsequently, the air passes through the atomizer 23, causing the therapeutic drug or liquid to enter the spray conduit 21; then, the therapeutic drug or liquid is sprayed out into the nasal cavity and treatment is achieved. In fact, the air suction and discharge actions occur almost at the same time. The operation of the spray occurs right after that of the aspirator, spraying liquid into the nasal cavity almost simultaneously when the mucus is sucked into the device.

The actions performed in this embodiment are the same as those in the first embodiment and are not to be repeated here.

Figure 7:
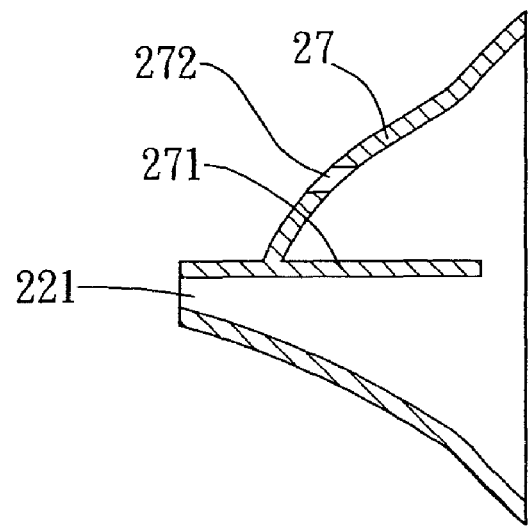
FIG. 7 is a cross-sectional view of the nozzle of the combined spray and aspirator device according to a first embodiment of the present invention.
Figure 8:
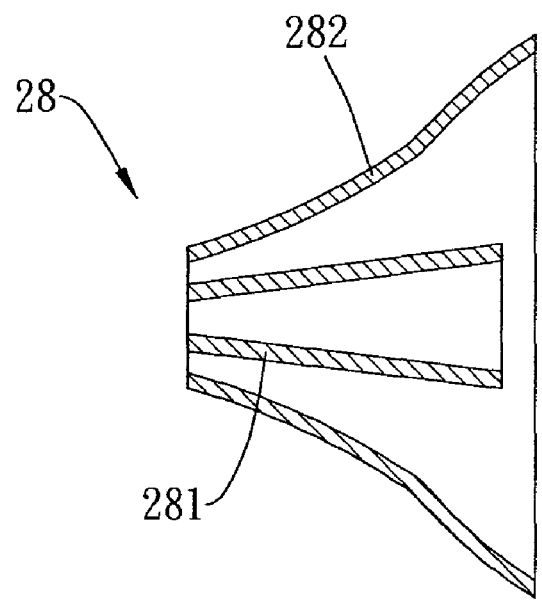
FIG. 8 is a cross-sectional view of the nozzle of the combined spray and aspirator device according to a second embodiment of the present invention.

Referring to FIGS. 7 and 8, cross-sectional views of a spray and aspirator nozzle of the combined nasal spray and aspirator device respectively according to a first and a second embodiment of the present invention are shown. As shown in FIGS. 4 and 7, the spray and aspirator assembly 20 comprises a spray and aspirator nozzle 27 mounted at the front end of both the spray conduit 21 and the first aspiration conduit 22. The spray and aspirator nozzle 27 is separated by a partition plate 271 so as to form a spray outlet 272 of the spray conduit 21, and to form an aspiration inlet 221 of the first aspiration conduit 22. Since the spray conduit 21 and the first aspiration conduit 22 are positioned alongside within the spray and aspirator nozzle 27, it is convenient for the user to insert the nozzle 27 of the spray and aspirator assembly 20 into the nasal cavity. It is convenient for the user to complete spray and aspiration operations almost simultaneously by spraying liquid into the nasal cavity and suctioning the cleansed liquid at the same time, as shown in FIG. 7. The spray and aspirator nozzle 27 has a spray outlet 272 that communicates with the liquid spray channel 232 of the atomizer 23 by means of a tube 233. This avoids spraying most of the liquid onto the inner wall of the spray and aspirator nozzle 27 during operation.

As shown in FIGS. 5 and 8, the spray and aspirator assembly 20 further comprises a spray and aspirator nozzle 28 mounted at the front end of both the spray conduit 21 and the first aspiration conduit 22 which are concentrically positioned, i.e., the spray conduit 21 surrounds the first aspiration conduit 22. Therefore, the spray and aspirator nozzle 28 is also of a concentric design, including an inner duct 281 and an outer duct 282. The ducts are concentrically positioned, the duct 281 serving as the inlet of the first aspiration conduit 22 and the duct 282 serving as the outlet of the spray conduit 21. Since the spray conduit 21 and the first aspiration conduit 22 are positioned concentrically, it is convenient for the user to insert the spray and aspirator nozzle 28 into the nasal cavity. Liquid is sprayed from the outer surrounding spray conduit 21 into the nasal cavity, and almost simultaneously, or alternately and continually, or alternately and uninterruptedly, the liquid is suctioned back into the inner surrounded first aspiration conduit 22, as indicated in FIG. 8.

In conclusion, the present invention integrates the functions of a nasal spray and a nasal aspirator. By spraying on the nasal cavity first, the device liquefies the mucus within, and almost simultaneously, it sucks the mucus away. The design of the present invention is physically more favorable for users, and therefore a patent application is brought out in accordance with the law.

What is claimed is:

1. A combined nasal spray and aspirator device, comprising:
    a housing including an air pump, at which an air suction connector and an air discharge connector are disposed, and the air pump is driven by a driving component to complete the air suction and discharge operations simultaneously; and
    a spray and aspirator assembly coupled to the air suction connector and the air discharge connector, comprising a spray conduit, a first aspiration conduit and a second aspiration conduit, wherein the spray conduit connects to an atomizer and the first aspiration conduit connects to a mucus collector so that when some air carrying mucus enters the mucus collector from said first aspiration conduit, the mucus is left in the collector and the air continues its progression through said second aspiration conduit, said air suction connector, said air discharge connector and said spray conduit to be sprayed out with therapeutic liquid.

2. The combined nasal spray and aspirator device according to claim 1, wherein the air pump comprises:
    a valve including an air suction hole having a first valve and an air discharge hole having a second valve, wherein the first valve is parallel to the second valve;
    a cover portion at which an air suction connector and an air discharge connector are disposed, further including a connection socket for connecting with the valve so that the first valve spatially corresponds to the air suction connector and the second valve spatially corresponds to the air discharge connector;
    a joint portion including an air hole which links to a channel and spatially corresponds to the second valve, wherein one end of the channel spatially corresponds to the first valve, and including a recess chamber formed corresponding to the channel at the opposite side of the joint portion; and
    a base portion at which a flexible plate is located, forming an air chamber altogether with the recess chamber.

3. The combined nasal spray and aspirator device according to claim 2, wherein an eccentric shaft is disposed at the driving component and the shaft is disposed in a pivot joint within the flexible plate.

4. The combined nasal spray and aspirator device according to claim 3, wherein the driving component is a motor.

5. The combined nasal spray and aspirator device according to claim 1, wherein the liquid inside is some water or therapeutic drug.

6. The combined nasal spray and aspirator device according to claim 1, wherein a passage is disposed between the atomizer and the liquid storage container.

7. The combined nasal spray and aspirator device according to claim 6, wherein the atomizer is connected to a liquid spray channel with the internal diameter less than that of the spray conduit, and the liquid spray channel communicates vertically with the passage.

8. The combined nasal spray and aspirator device according to claim 6, wherein the atomizer and the passage are disposed at the front end of the spray conduit.

9. The combined nasal spray and aspirator device according to claim 1, wherein the liquid storage container has a filling inlet.

10. The combined nasal spray and aspirator device according to claim 1, wherein the spray conduit and the first aspiration conduit are positioned alongside.

11. The combined nasal spray and aspirator device according to claim 1, wherein the spray conduit and the first aspiration conduit are concentrically positioned.

12. The combined nasal spray and aspirator device according to claim 1, wherein the housing comprises a power chamber for placing a battery covered with a lid.

13. The combined nasal spray and aspirator device according to claim 1, wherein the spray and aspirator assembly further comprises a spray and aspirator nozzle mounted at the front end of both the spray conduit and the first aspiration conduit, the spray and aspirator nozzle being separated by a partition plate so as to form a spray outlet of the spray conduit and to form an aspiration inlet of the first aspiration conduit.

14. The combined nasal spray and aspirator device according to claim 13, wherein the outlet of the spray and aspirator nozzle is a spray outlet communicating with the liquid spray channel of the atomizer by means of a tube.

* * * * *